United States Patent
Harbison

(10) Patent No.: US 9,211,129 B2
(45) Date of Patent: Dec. 15, 2015

(54) IMPLANT AND RELATED SURGICAL TECHNIQUE FOR USE IN HIGH TIBIAL OSTEOTOMY

(71) Applicant: BIOMET SPORTS MEDICINE, LLC, Warsaw, IN (US)

(72) Inventor: Kyle Harbison, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 273 days.

(21) Appl. No.: 13/957,502

(22) Filed: Aug. 2, 2013

(65) Prior Publication Data
US 2015/0038974 A1 Feb. 5, 2015

(51) Int. Cl.
*A61F 2/28* (2006.01)
*A61B 17/17* (2006.01)
*A61F 2/30* (2006.01)

(52) U.S. Cl.
CPC ........... *A61B 17/1764* (2013.01); *A61F 2/2846* (2013.01); *A61F 2002/30266* (2013.01); *A61F 2230/0013* (2013.01)

(58) Field of Classification Search
CPC .................. A61F 2002/285; A61F 2002/2853; A61F 2002/30266; A61F 2002/30736; A61F 2002/3892; A61F 2002/30112; A61F 2002/30538; A61F 17/8095; A61F 17/151; A61F 17/809; A61F 2230/0013; A61F 2250/0006
See application file for complete search history.

(56) References Cited

U.S. PATENT DOCUMENTS

| 6,423,061 | B1 | 7/2002 | Bryant |
| 8,496,662 | B2 | 7/2013 | Novak et al. |
| 2010/0070037 | A1* | 3/2010 | Parry et al. ................. 623/17.16 |

OTHER PUBLICATIONS

Arthroscopyjournal, "HTO With Aescula", https://www.youtube.com/watch?v=PF1Ke_Vm7yg, Jun. 12, 2013.
Biomet, "DFS Angular Hinge Fixator System", http://www.biomet.com/trauma/products.cfm?pdid=4&majcid=28&prodid=261, 2014.
Zimmer, Inc., "Zimmer Natural-Knee II CoCr Revision Baseplate Surgical Technique", 2008.
Arthrex, Inc., "Opening Wedge Osteotomy System Using ContourLock HTO Plates Surgical Technique", 2011.
Ebi, L.P., "DynaFix VS Osteotomy System Surgical Technique", Parsippany, NJ, Oct. 2002.
Arthrex, Inc., "iBalance HTO System for Medical High Tibial Opening Wedge Osteotomy Surgical Technique", 2013.

* cited by examiner

*Primary Examiner* — David Bates
*Assistant Examiner* — Samuel Hanna
(74) *Attorney, Agent, or Firm* — Schwegman Lundberg & Woessner, P.A.

(57) ABSTRACT

An implant for use in high tibial osteotomy can include a central implant portion, a first side implant portion and a second side implant portion. The first and second side implant portions can be selectively rotatable relative to each other. A method of performing high tibial osteotomy can include providing an implant having a superior surface and an inferior surface. The first superior surface and the second inferior surface can define an implant angle therebetween. A correction angle of the tibia can be determined. A first cut can be made in the tibia. An angle of a second cut relative to the first cut can be determined based on a difference between the implant angle and the correction angle. The second cut can be made in the tibia. The tibia can be opened creating an opening for receipt of the implant. The implant can be inserted into the opening.

6 Claims, 8 Drawing Sheets

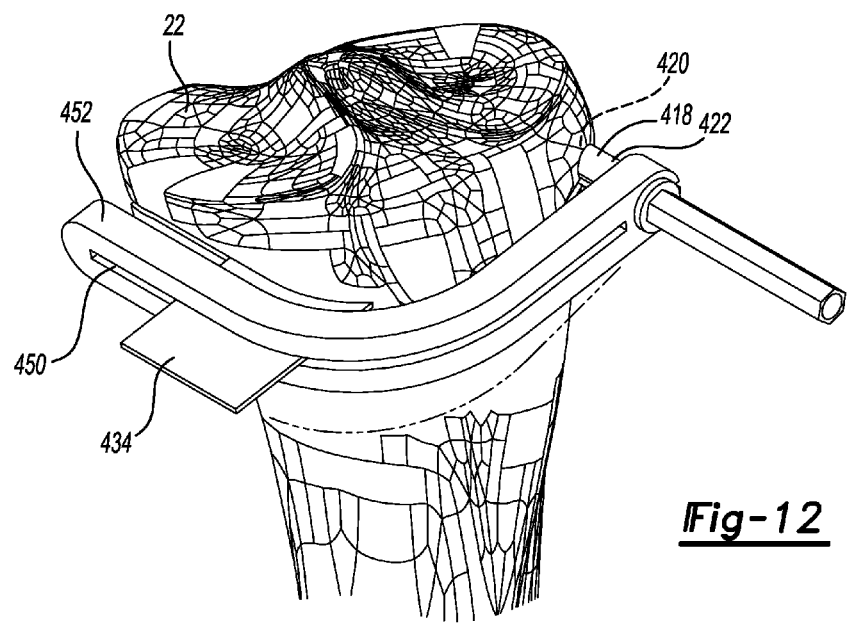
Fig-12
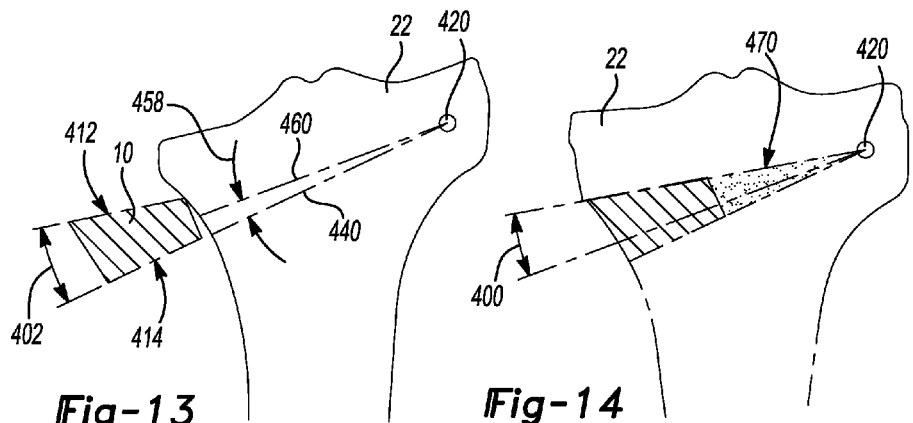
Fig-13
Fig-14

IMPLANT AND RELATED SURGICAL TECHNIQUE FOR USE IN HIGH TIBIAL OSTEOTOMY

FIELD

The present disclosure relates generally to high tibial osteotomy. More particularly, the present disclosure relates to an implant and related technique for use in high tibial osteotomy.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

High tibial osteotomy is a surgical procedure used to correct a malalignment in a tibia. Malalignment in a tibia can accelerate wear in the lateral or medial compartments of the knee and lead to degeneration. Malalignment can include a varus deformation or a "bow-legged" knee condition and a valgus deformation or a "knock-knee" condition. In this regard, a varus knee can cause the protective tissues of the knee to wear more on a medial aspect of the knee. Similarly, a valgus knee can cause the protective tissues of the knee to wear more on the lateral aspect of the knee. In either scenario, it is desirable to perform a high tibial osteotomy to correct the malalignment and position the tibia in a more neutral orientation.

In one procedure, a varus deformation can be corrected by making a single cut in the medial tibia. The tibia is opened and an implant is positioned within the opening. In another procedure, a valgus deformation can be corrected by making a pair of cuts in the medial tibia and removing a wedge of tibial bone. After the wedge of tibial bone is removed, the void is closed.

When performing a procedure to correct a varus deformation, typically a surgeon would need to select an implant from a set of implants that has an implant angle suitable for the needs of a particular patient. A large inventory of implants are typically necessary to accommodate a wide range of patients. Furthermore, some implants may not match a profile of the patient's tibia in the transverse plane. In this regard, a need exists to provide a more universal implant suitable for use with a wide range of patients and related method for performing high tibial osteotomy.

SUMMARY

This section provides a general summary of the disclosure, and is not a comprehensive disclosure of its full scope or all of its features.

An implant for use in high tibial osteotomy can include a central implant portion, a first side implant portion and a second side implant portion. The first and second side implant portions can be selectively rotatable relative to each other.

In one configuration, the first and second implant portions can be hingedly coupled relative to each other. The first side implant portion can include a first hinge arm that defines a first passage therein. The second side implant portion can include a second hinge arm that defines a second passage therein. The implant can further include a hinge post received by the first and second passages. The first and second implant portions can be configured to rotate about the hinge post.

In additional configurations, the central implant portion can include an arcuate body having an outer arcuate portion and an inner arcuate portion. The central implant can comprise a central solid portion and a central porous portion. The central solid portion can be disposed on the outer arcuate portion. The central porous portion can be disposed on the inner arcuate portion. The first side implant portion can include a first outer solid portion and a first inner porous portion. The first hinge arm can be provided exclusively by the first outer solid portion. The second side implant portion can include a second outer solid portion and a second inner porous portion. The second hinge arm can be provided exclusively by the second outer solid portion. In one example, the first and second side implant portions can be rotatably coupled to each other at a living hinge.

An implant for use in high tibial osteotomy can include a central implant portion, a first side implant portion and a second side implant portion. The central implant portion can have an arcuate body including a central solid portion and a central porous portion. The central solid portion can include a hinge post. The first side implant portion can have a first outer solid portion and a first inner porous portion. The first outer solid portion can include a first hinge arm that is rotatably coupled to the hinge post. The second side implant portion can have a second outer solid portion and a second inner porous portion. The second outer solid portion can include a second hinge arm that is rotatably coupled to the hinge post. The first and second side implant portions can be selectively rotatably coupled relative to each other.

According to other features, the central implant portion can further comprise a first upper wing connected to a first lower wing by a first central wall. The first upper wing, the first lower wing and the first central wall can define a first recess. The central implant can further include a second upper wing connected to a second lower wing by a second central wall. The second upper wing, the second lower wing and the second central wall can define a second recess.

According to additional features, the arcuate body of the central implant portion can include a convex central side and a concave central side. The first and second central walls can taper toward the convex central side. The first side implant portion can be at least partially received by the first recess. The second side implant portion can be at least partially received by the second recess. The implant can be formed as one unit by laser sintering.

A method of performing high tibial osteotomy according to the present disclosure can include providing an implant having a first superior surface and a second inferior surface. The first superior surface and the second inferior surface can define an implant angle therebetween. A correction angle of the tibia can be determined. A first cut can be made in the tibia. An angle of a second cut relative to the first cut can be determined based on a difference between the implant angle and the correction angle. The second cut can be made in the tibia. The tibia can be opened creating an opening for receipt of the implant. The implant can be inserted into the opening.

According to other features, a relief hole can be drilled into the tibia with a coring drill. A blade can be advanced through a slot in a guide arm. The blade can be advanced through a keyway defined in the coring drill. At least one of autograph and allograph bone matrix can be deposited into the opening prior to inserting the implant into the opening. The coring drill can remain at one position during the making of the first and second cuts.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 12 is a medial view of the left tibia of FIG. 10 shown with the guide arm rotated to a second position and the blade making a second cut;

FIG. 13 is an anterior view of the left tibia of FIG. 10 shown with the implant positioned on a medial side ready for insertion into an opening of the tibia; and FIG. 14 is an anterior view of the left tibia of FIG. 12 shown with the implant advanced into the opening of the tibia.

DETAILED DESCRIPTION

The following description is merely exemplary in nature and is not intended to limit the present disclosure, its application, or uses. Although the following description is related generally to an implant for high tibial osteotomy, the implant and related technique is not so limited. In this regard, while the following discussion will be directed toward correcting a malalignment in a tibia, the same may be applied to correcting a malalignment in other long bones.

Figure 1:
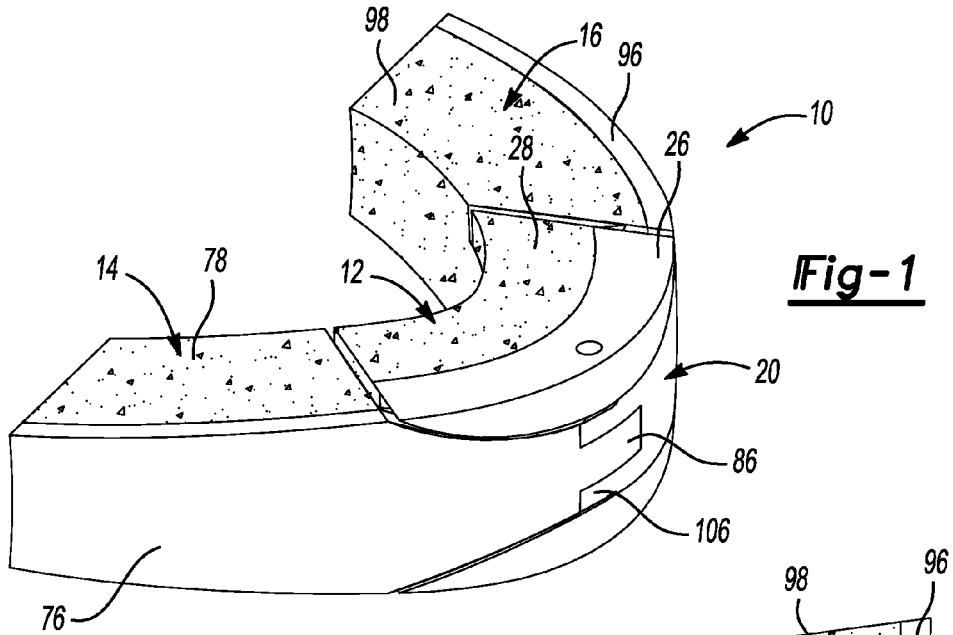
FIG. 1 is a front perspective view of an implant for use in high tibial osteotomy constructed in accordance to one example of the present disclosure.
Figure 2:
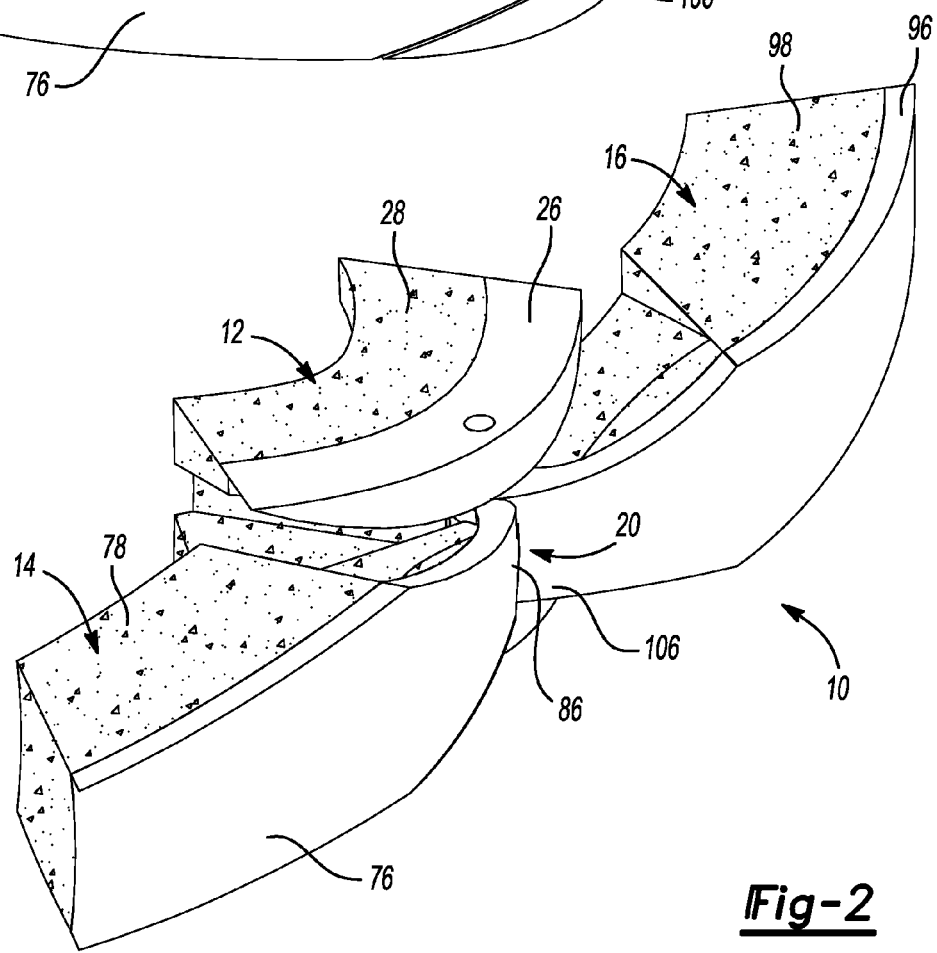
FIG. 2 is a front perspective view of the implant of FIG. 1 and shown with a first and second side implant portions rotated relative to each other about a hinge.

With initial reference to FIGS. 1 and 2, an implant for high tibial osteotomy constructed in accordance to the present disclosure is shown and generally identified as implant 10. As will become appreciated by the following discussion, the implant 10 may be used during a high tibial osteotomy procedure to correct a malalignment in a tibia. The implant 10 can generally include a central implant portion 12, a first side implant portion 14 and a second side implant portion 16. The implant 10 can further include a hinge 20 that can allow the first side implant portion 14 and the second side implant portion 16 to selectively rotate relative to each other. While the first and second side implant portions 14 and 16 are shown rotated outwardly an exemplary amount in FIG. 2, it will be appreciated that the first and second side implant portions 14 and 16 may be rotated outwardly any given amount to specifically match a profile of a patient's tibia 22 (FIG. 13) in a transverse plane. In this regard, the implant 10 can be adjustable to accommodate a tibial profile of a specific patient intraoperatively.

While the central implant portion 12, the first side implant portion 14 and the second side implant portion 16 are shown separately in FIGS. 3-7, they may be formed as a single unit such as during a laser sintering process. In this regard, as described herein, each of the central implant portion 12, the first side implant portion 14 and the second side implant portion 16 include both solid portions and porous portions. The respective solid and porous portions can be integrally formed during laser sintering. Explained further, the respective solid and porous portions need not be specifically coupled together from distinctly formed pieces. Moreover, the central implant portion 12, the first side implant portion 14 and the second side implant portion 16 can be formed as a hinged unit. In this regard, the central implant portion 12, the first side implant portion 14 and the second side implant portion 16 are not required to be specifically assembled together. In one example, the implant can be formed of biocompatible metal such as titanium, titanium alloys, cobalt, cobalt alloys, chromium, chromium alloys, tantalum, tantalum alloys, and stainless steel. Other materials are contemplated.

Figure 3:
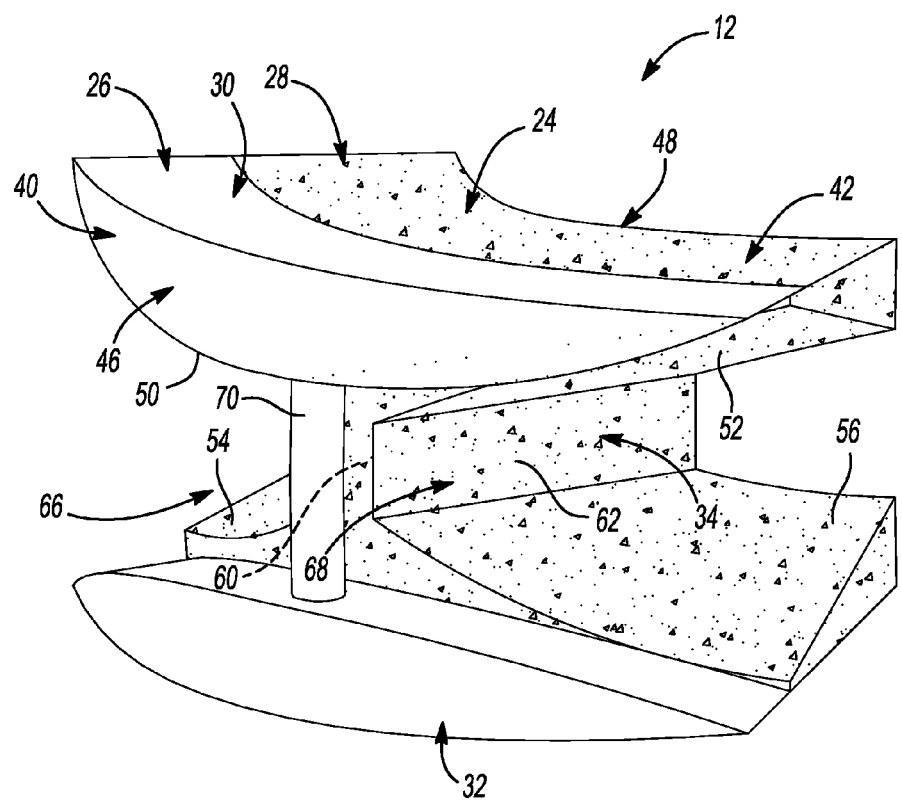
FIG. 3 is a front perspective view of a central implant portion of the implant shown in FIG. 1.

With additional reference now to FIG. 3, the central implant portion 12 will be further described. The central implant portion 12 generally includes an arcuate body 24 that generally includes a central solid portion 26 and a central porous portion 28. The arcuate body 24 can have an upper portion 30, a lower portion 32 and a connecting portion 34. The upper portion 30, the lower portion 32 and the connecting portion 34 of the arcuate body 24 can collectively provide an outer arcuate portion 40 and an inner arcuate portion 42. The outer arcuate portion 40 and the inner arcuate portion 42 can generally provide a convex central side 46 and a concave central side 48, respectively.

The upper portion 30 can include a first upper wing 50 and a second upper wing 52. The lower portion 32 can include a first lower wing 54 and a second lower wing 56. As shown in FIG. 3, the first and second upper wings 50 and 52 form a continuous sweeping geometry. Similarly, the first and second lower wings 54 and 56 form a continuous sweeping geometry.

The connecting portion 34 can include a first central wall 60 and a second central wall 62. The first and second central walls 60 and 62 can generally taper toward the convex central side 46. The first upper wing 50, the first lower wing 54 and the first central wall 60 can cooperate to form a first recess 66. The second upper wing 52, the second lower wing 56 and the second central wall 62 can cooperate to form a second recess 68. A hinge post 70 can generally extend between the upper portion 30 and the lower portion 32 near the outer arcuate portion 40. The hinge post 70 can be formed exclusively of solid material by the central solid portion 26.

Figure 4:
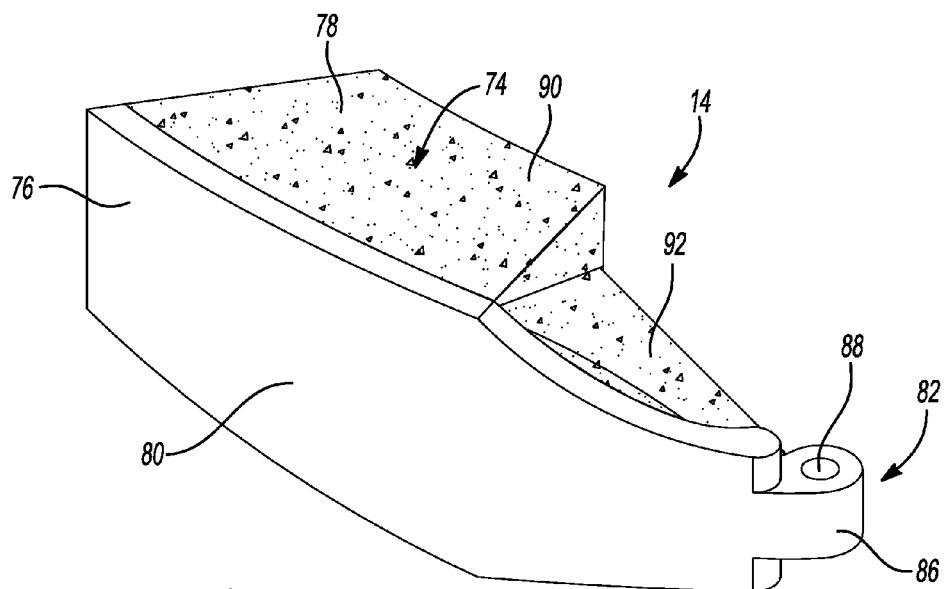
FIG. 4 is a front perspective view of the first side implant portion of the implant shown in FIG. 1.
Figure 5:
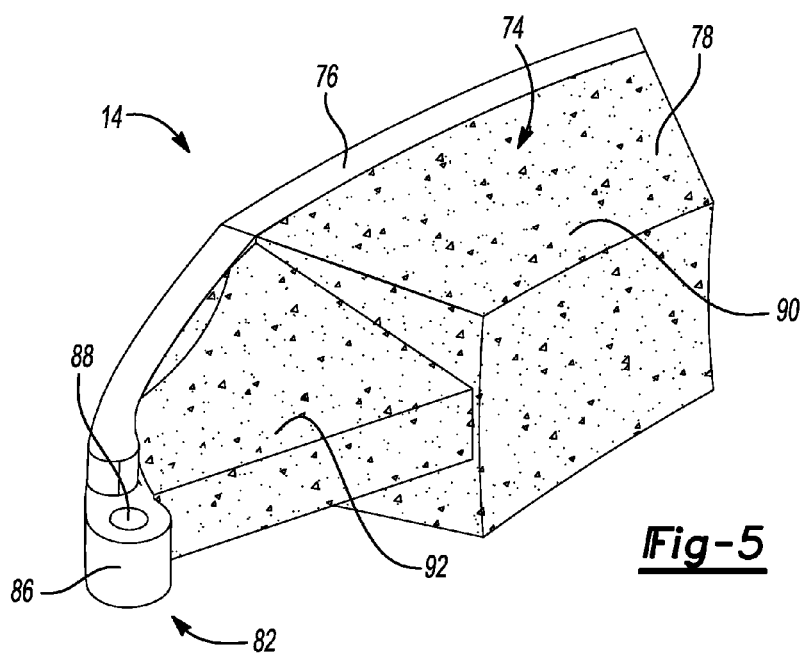
FIG. 5 is a rear perspective view of the first side implant portion shown in FIG. 4.

Turning now to FIGS. 4 and 5, the first side implant portion 14 will be further described. The first side implant portion 14 generally includes a first arcuate body 74 that generally includes a first solid portion 76 and a first porous portion 78.

The first solid portion 76 can include a first outer solid portion 80 and a first hinge portion 82. The first hinge portion 82 can include a first hinge arm 86 that defines a first passage 88. The first porous portion 78 can include a first inner porous portion 90 and a first wall 92.

Figure 6:
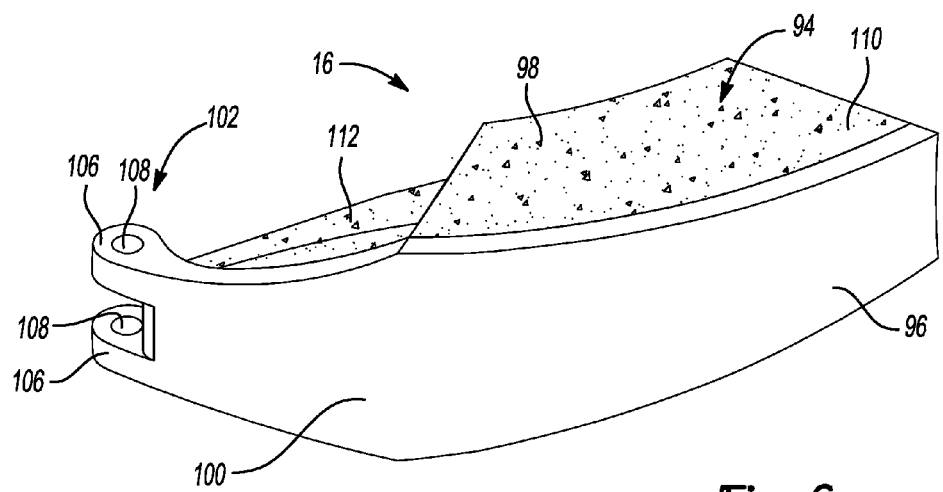
FIG. 6 is a front perspective view of a second side implant portion of the implant shown in FIG. 1.
Figure 7:
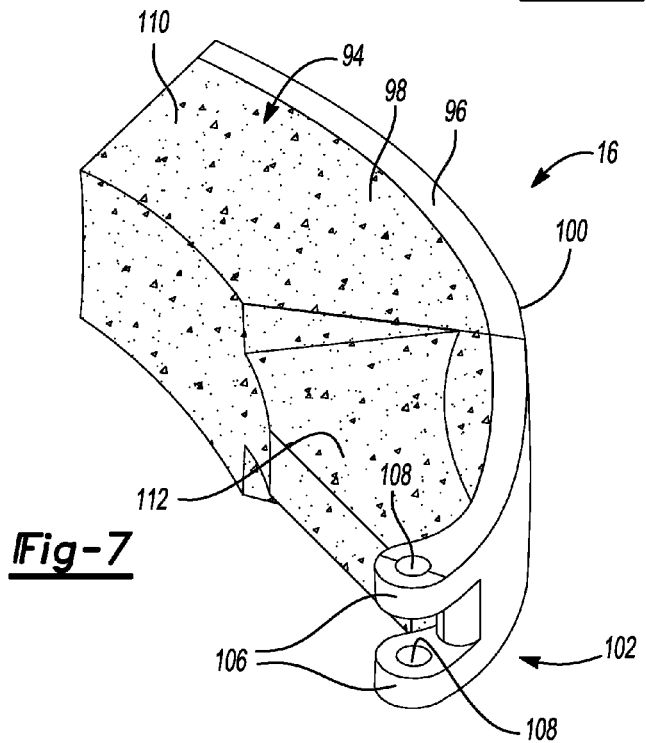
FIG. 7 is a rear perspective view of the second side implant portion of FIG. 6.

Turning now to FIGS. 6 and 7, the second side implant portion 16 will be further described. The second side implant portion 16 generally includes a second arcuate body 94 that generally includes a second solid portion 96 and a second porous portion 98. The second solid portion 96 can include a second outer solid portion 100 and a second hinge portion 102. The second hinge portion 102 can include a pair of second hinge arms 106 that collectively define a second passage 108. The second porous portion 98 can include a second inner porous portion 110 and a first wall 112.

With reference now to FIGS. 1-7, the geometries of the central implant portion 12, the first side implant portion 14 and the second side implant portion 16 will be described. In general, the first wall 92 (FIG. 4) of the first side implant portion 14 can be nestingly received by the first recess 66 (FIG. 3) of the central implant portion 12. The hinge post 70 can be received by the first passage 88 of the first hinge arm 86. The second wall 112 (FIG. 7) of the second side implant portion 16 can be nestingly received by the second recess 68 (FIG. 3) of the central implant portion 12. The hinge post 70 can be received by the pair of second passages 108 of the respective second hinge arms 106. The first hinge arm 86 can be received between the pair of second hinge arms 106 (FIG. 1). It will be appreciated that the configuration of the hinge 20 is merely exemplary. In this regard, while the first side implant portion 14 is shown having one hinge arm 86 and the second side implant portion 16 is shown having two hinge arms 106, the configuration may be reversed. Alternatively, each of the first and second hinge arms 86 and 106 may be formed of one or more hinge arms. Moreover, while the hinge post 70 has been described as part of the central implant 12, the hinge post 70 may additionally or alternatively be incorporated on the first or second implant portion 14 or 16.

Figure 8:
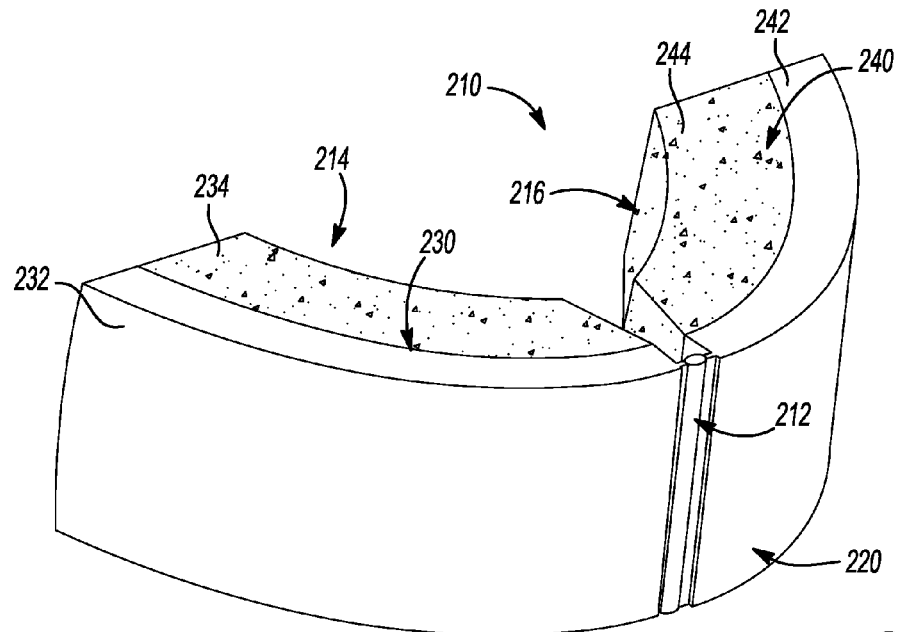
FIG. 8 is a front perspective view of an implant for use in high tibial osteotomy and constructed in accordance to additional features of the present disclosure.

With reference now to FIG. 8 an implant constructed in accordance to additional features of the present disclosure is shown and generally identified at reference 210. The implant 210 can generally include a central implant portion 212, a first side implant portion 214 and a second side implant portion 216. The implant 210 can further include a hinge 220 that allows the first side implant portion 214 and the second side implant portion 216 to selectively rotate relative to each other. The hinge 220 of the implant 210 can include a living hinge. In this regard, the hinge 220 can deform to allow the first and second side implant portions 214 and 216 to rotate relative to each other.

The first side implant portion 214 generally includes a first arcuate body portion 230 that includes a first solid portion 232 and a first porous portion 234. The second side implant portion 216 generally includes a second arcuate body portion 240 that includes a second solid portion 242 and a second porous portion 244. The first solid portion 232, the second solid portion 242 and the living hinge 212 can be formed of biocompatible metal. In this regard, the living hinge 212 can be a metal living hinge. Again, as with the implant 10 described above, the first and second side implant portions 214 and 216 can rotate about the living hinge 212 to any given position to specifically match a profile of a patient's tibia 22 (FIG. 13) in the transverse plane.

Figure 9:
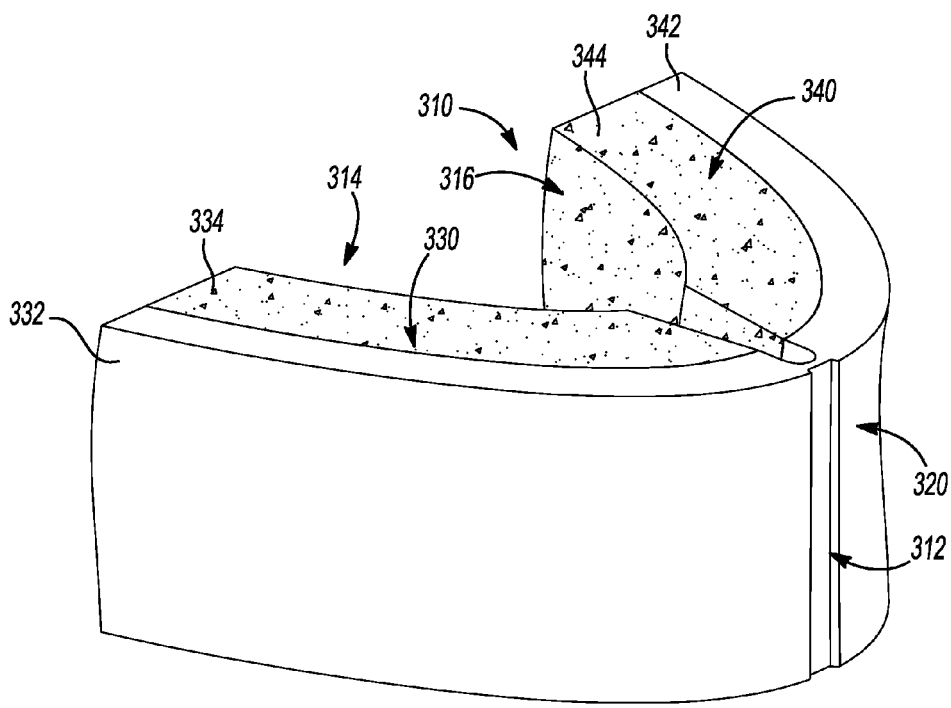
FIG. 9 is a front perspective view of an implant for use in high tibial osteotomy and constructed in accordance to other features of the present disclosure.
Figure 10:
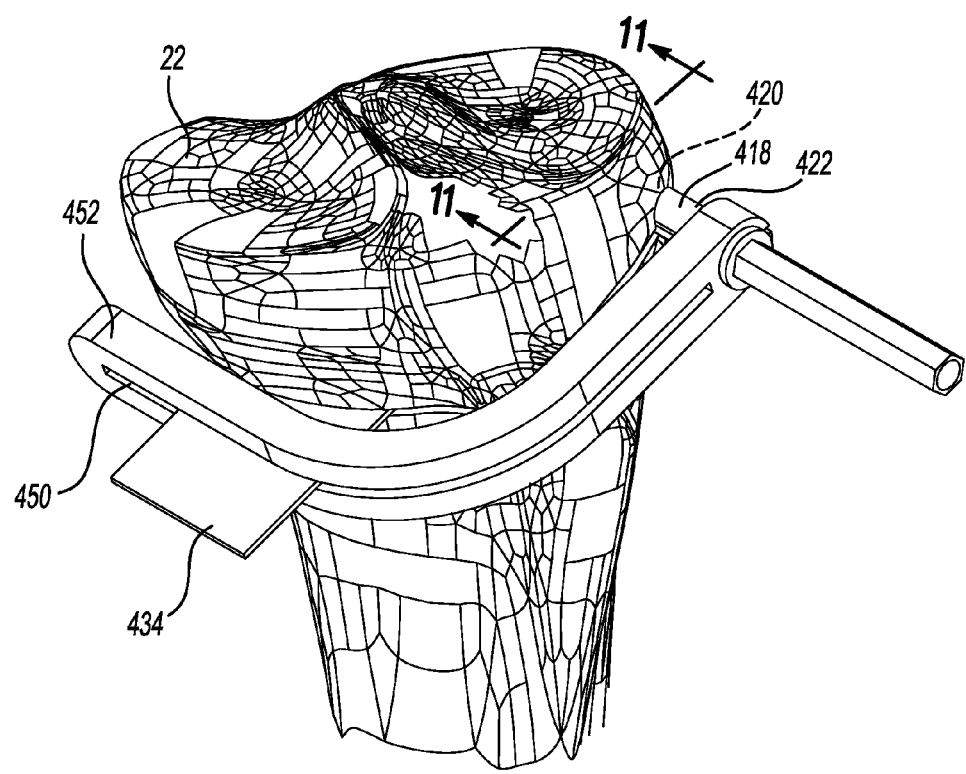
FIG. 10 is a medial view of a left tibia shown with a guide arm in a first position and a blade making a first cut during a high tibial osteotomy procedure according to the present disclosure.
Figure 11:
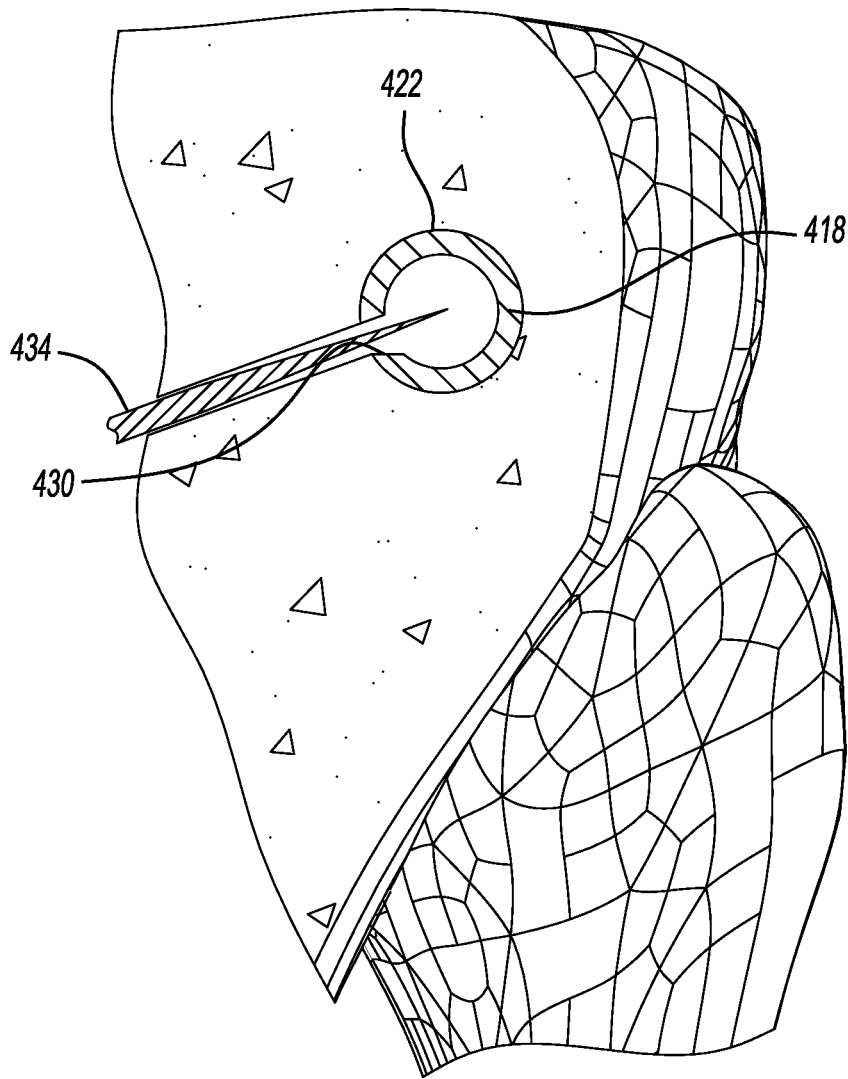
FIG. 11 is a cross-sectional view of the tibia taken along lines 11-11 of FIG. 10.

With reference now to FIG. 9 an implant constructed in accordance to additional features of the present disclosure is shown and generally identified at reference 310. The implant 310 can generally include a central implant portion 312, a first side implant portion 314 and a second side implant portion 316. The implant 310 can further include a hinge 320 that allows the first side implant portion 314 and the second side implant portion 316 to selectively rotate relative to each other. The hinge 320 of the implant 310 can include a living hinge. In this regard, the hinge 320 can deform to allow the first and second side implant portions 314 and 316 to rotate relative to each other.

The first side implant portion 314 generally includes a first arcuate body portion 330 that includes a first solid portion 332 and a first porous portion 334. The second side implant portion 316 generally includes a second arcuate body portion 340 that includes a second solid portion 342 and a second porous portion 344. The first solid portion 332, the second solid portion 342 and the living hinge 312 can be formed of polymeric material such as ultra high molecular weight polyethylene. In this regard, the living hinge 312 can be a polymeric or plastic living hinge. Again, as with the implant 10 described above, the first and second side implant portions 314 and 316 can rotate about the living hinge 312 to any given position to specifically match a profile of a patient's tibia 22 (FIG. 13) in the transverse plane.

With additional reference now to FIGS. 10-14, an exemplary technique for high tibial osteotomy will be described. In general, the femoral-tibial alignment angle is desirable between 7 and 13 degrees. In the example shown, the tibia is a left tibia having a varus deformation. In this regard, the high tibial osteotomy discussed below will be performed to correct a "bow-legged" malformation. It will be appreciated that the implants and techniques described herein can be also applied for a valgus deformation to correct a "knock-kneed" malformation. To correct the varus deformation, the implant 10 can be advanced into an opening created on the medial side of the tibia 22 (FIGS. 13 and 14).

At the outset, a surgeon can determine a correction angle 400 of the tibia 22. In the example shown, the correction angle 400 (FIG. 14) of the tibia 22 will be 10 degrees. In this regard, the medial side of the tibia will be raised 10 degrees. Next, an implant angle 402 (FIG. 13) of the implant 10 can be determined. The implant angle 402 can be an angle between a superior surface 412 of the implant 10 and an inferior surface 414 of the implant. In the example provided, the implant angle 402 is 15 degrees. As will become appreciated, a modular implant 10 having an implant angle 402 of 15 degrees can be used in a variety of examples to correct various valgus and varus deformations. In this way, a modular implant 10 can be used for correcting malalignments on tibias for a wide range of patients.

Next, a cannulated coring drill 418 can be used to create a relief or datum hole 420 in the tibia 22. The coring drill 418 can have a coring drill collar 422 that defines a keyway 430. A blade 434 can then be used to make a first cut 440 (FIG. 13) in the tibia 22. In one example, the blade 434 can be guided through a slot 450 defined in a guide arm 452 pivotally coupled to the coring drill 418. The datum hole 420 acts as a datum axis, which can constrain the guide arm and blade 434 across all degrees of freedom except rotation on the coronal plane.

Notably, the depth of cut in the lateral direction is limited by the coring drill collar 422. Explained further, the blade 434 can be received by the keyway 430 (FIG. 11) and inhibited from advancing further into the tibia 22 by the collar 422. Other geometries of the keyway 430 are contemplated for inhibiting further lateral advancement of the blade 434. The keyway 430 on the coring drill collar 422 can also catch debris created while advancing the blade 434 toward the coring drill collar 422.

After the first cut 440 has been made, an angle 458 of a second cut 460 (relative to the first cut 440) can be determined. The angle of the second cut 460 will be the implant angle 400 (in this example 15 degrees) minus the angle of correction (in this example 10 degrees). The angle of the second cut 460 (relative to the first cut 440) in this example is 5 degrees.

The guide arm 452 can then be rotated about the drill 418 to the angle 458 of the second cut. In one example indicia can be provided on the guide arm and/or the coring drill collar 422 to assist in attaining the angle 458. The second cut 460 can then be made using the blade 434. Again, as with the first cut 440, the blade 434 can be received by the keyway 430 to inhibit further advancing of the blade 434 into the tibia.

After the second cut 460 has been made, the blade 434, guide arm 452 and coring drill 418 can be removed from the tibia. The tibia can then be "opened" to receive the implant 10. The implant 10 can then be advanced into the opening. In some examples, the first and second side implant portions 14 and 16 can be rotated to substantially match an outer profile of the tibia in the transverse plane. As such, the implant 10 can address patient variability in the anterior-posterior direction. Bone filler 470 such as allograft, autograft or xenograft material can be optionally disposed inboard of the implant 10.

As can be appreciated, the present teachings provide a single implant 10, 210 or 310 that can be applicable for all tibial correction angles. In this way, the tibia 22 can be cut in any manner suitable to accommodate the implant 10 while still attaining any correction angle.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An implant for use in high tibial osteotomy, the implant comprising:
    a central implant portion having an arcuate body including a central solid portion and a central porous portion, the central solid portion including a hinge post, wherein the central implant portion has (i) a central superior surface that extends from the central solid portion to the central porous portion and (ii) a central inferior surface that extends from the central solid portion to the central porous portion;
    a first side implant portion having a first outer solid portion and a first inner porous portion, the first outer solid portion including a first hinge arm that is rotatably coupled to the hinge post, wherein the first side implant portion has (i) a first superior surface that extends from the first outer solid portion to the first inner solid portion and (ii) a first inferior surface that extends from the first outer solid portion to the first inner solid portion; and
    a second side implant portion having a second outer solid portion and a second inner porous portion, the second outer solid portion including a second hinge arm that is rotatably coupled to the hinge post, wherein the second side implant portion has (i) a second superior surface that extends from the second outer solid portion to the second inner solid portion and (ii) a second inferior surface that extends from the second outer solid portion to the second inner solid portion;
    wherein the central implant portion, the first side implant portion and the second side implant portions are selectively rotatably coupled relative to each other and all of the central superior surface, the first superior surface, the second superior surface, the central inferior surface, the first inferior surface and the second inferior surface define taper opposing superior and inferior surfaces from respective solid to porous portions and configured to be inserted between and engage superior and inferior bone portions to correct malalignment in a tibia.

2. The implant of claim 1 wherein the central implant portion further comprises:
    a first upper wing connected to a first lower wing by a first central wall, the first upper wing, the first lower wing and the first central wall defining a first recess; and
    a second upper wing connected to a second lower wing by a second central wall, the second upper wing, the second lower wing and the second central wall defining a second recess.

3. The implant of claim 2 wherein the arcuate body of the central implant portion includes a convex central side and a concave central side.

4. The implant of claim 3 wherein the first and second central walls taper toward the convex central side.

5. The implant of claim 3 wherein the first side implant portion is at least partially received by the first recess and wherein the second side implant portion is at least partially received by the second recess.

6. The implant of claim 1 wherein the implant is formed as one unit by laser sintering.

* * * * *